United States Patent [19]

Marando

[11] Patent Number: Plant 6,913

[45] Date of Patent: Jul. 11, 1989

[54] MARANDO WEEPING HONEY LOCUST

[75] Inventor: Vincent Marando, Bayside, N.Y.

[73] Assignee: Speer & Sons Nursery, Inc., Woodburn, Oreg.

[21] Appl. No.: 141,611

[22] Filed: Jan. 7, 1988

[51] Int. Cl.[4] ..... A01H 5/00
[52] U.S. Cl. ..... Plt./52
[58] Field of Search ..... Plt./52

[56] References Cited

PUBLICATIONS

Hilliers Manual of Trees & Shrubs, 2nd Ed., 1979, A. S. Barnes and Co., p. 132.

*Primary Examiner*—Robert E. Bagwill
*Attorney, Agent, or Firm*—Charles W. Rummler

[57] ABSTRACT

A new variety of honey locust tree particularly characterized by its seedless, non-flowering, non-fruiting and rapid growth and its numerous, long, pendulous branches which bend outwardly from the trunk and then hang downward some hanging substantially to the ground.

1 Drawing Sheet

BACKGROUND OF THE NEW PLANT

This new honey locust variety was discovered by me among a group of seedlings grown from seeds gathered from various locust trees and planted in 1974 in greenhouse at my nursery in Manorville, N.Y. About two years later, I transplanted approximately sixty-five of these seedlings to my nursery at Holtsville, Long Island, and during the course of the following growing season, I noticed that one of the honey locust whips had a pendulous branching habit whereas none of the other plants had grown with this particular character. This pendulous honey locust plant was staked to a ten to twelve foot bamboo pole and tied every six inches to assist the plant to grow vertically.

As this particular tree grew vertically, the branches continued to grow outwardly and then pendulously toward the ground. When the tree attained a two inch caliper, it was transplanted to my residence in Bayside, Long Island, where the plant continued to grow, amongst larger, mature trees, in the same "weeping" pendulous manner. It was noted, however, that there was no indication of any flowering or seeds and that there were no thorns. Cuttings from the parent plant grown both at my nursery at Manorville, N.Y., and at my Holtsville, Long Island, nursery, through several successive generations, demonstrated in every case that the new trees had reproduced all of the distinctive characteristics of the original plant showing that these novel characteristics would hold true from generation to generation and appeared to be firmly fixed.

This new tree is being propagated by budding at the nursery of Speer & Sons at Hillsboro, Oreg.

DESCRIPTION OF THE DRAWINGS

My new weeping honey locust is illustrated by the accompanying drawings, of which the upper view shows a twelve foot tree at about three years illustrating its general form and nature; and the lower view is a close-up picture of the same tree showing more of its actual detail.

DESCRIPTION OF THE NEW PLANT

The following is a detailed description of one of my new "weeping" honey locust variety as grown at Hillsboro, Oreg., the tree being about eight years old.

THE PLANT

Origin: Seedling.
Parentage: Unknown.
Classification:
- *Botanic.*—*Gleditsia triacanthus* inermis.
- *Commercial.*—Weeping Honey Locust.

Form: Tree.
Height: Averaging about 15 to 20 feet.
Trunk size: About 5 inches caliper for a tree of about 15 feet in height.
Bark: Smooth and deep brown in color.
Growth rate: Fast and very hardy.
Branching:
- *Quantity.*—Abundant.
- *Angle of attachment.*—About 60° from the trunk.
- *Spacing.*—From 6 to 12 inches.
- *Size.*—The branches range from about two to five feet long under nursery growing conditions.
- *Type.*—Pendulous.

Leaves:
- *Quantity.*—Abundant.
- *Size.*—Length: About 10 inches, on average. Width: About 9 inches, on average.
- *Form.*—Double-compound.
- *Texture.*—Smooth.
- *Color.*—Upper side — Dark green. Under side — Lighter green.
- *Leaflets.*—Number: About 120 per leaf. Size: About ¾ inch long and about ⅜ inch wide.
- *Petioles.*—Length: About 2 to 3 inches.

I claim:

1. The new and distinct variety of honey locust and the parts thereof, substantially as herein shown and described, characterized by its vigorous, rapid growth habit and its abundant foliage with pendulous branches, some hanging substantially to the ground.

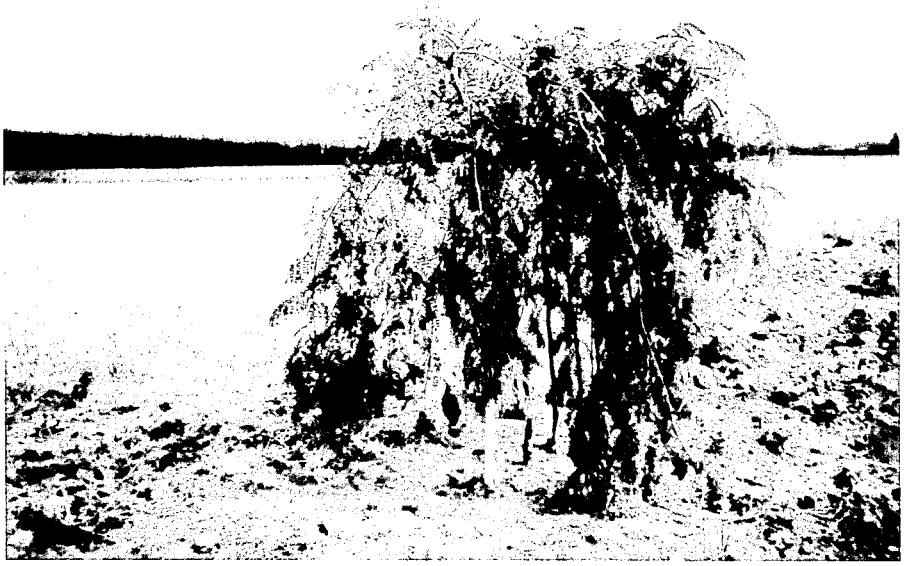
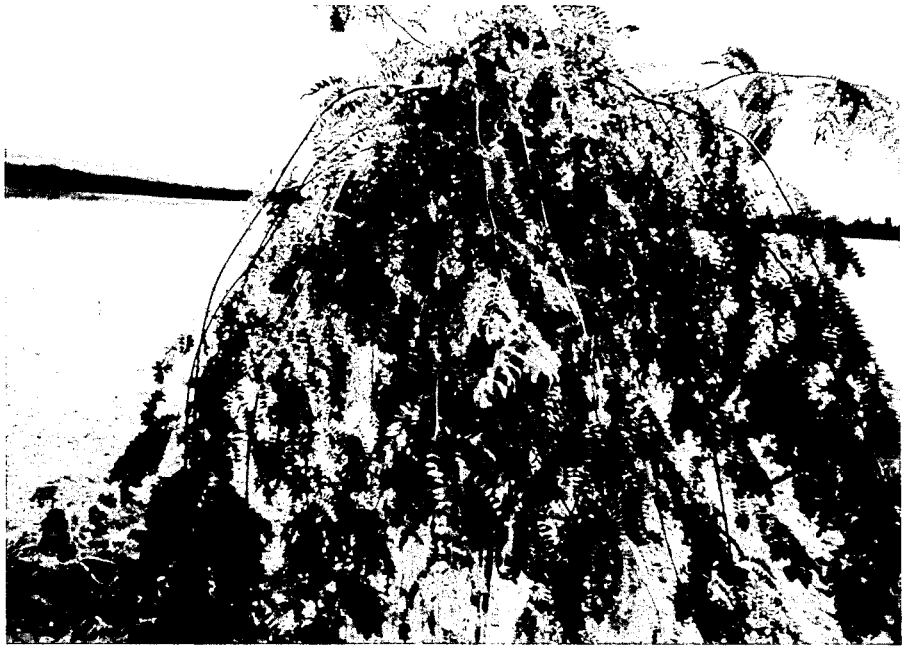

* * * * *